United States Patent [19]

Manara et al.

[11] 4,177,167

[45] Dec. 4, 1979

[54] CATALYST FOR THE PREPARATION OF DIMETHYL ETHER

[75] Inventors: Giovanni Manara; Bruno Notari; Vittorio Fattore, all of San Donato Milanese, Italy

[73] Assignee: Snamprogetti S.p.A., Milan, Italy

[21] Appl. No.: 862,575

[22] Filed: Dec. 20, 1977

[30] Foreign Application Priority Data

Dec. 23, 1976 [IT] Italy .............................. 30800A/76

[51] Int. Cl.$^2$ ............................................. B01J 21/12
[52] U.S. Cl. ............................ 252/455 R; 260/449 R
[58] Field of Search .................. 252/455 R, 462, 453; 260/449 R

[56] References Cited

U.S. PATENT DOCUMENTS

| | | | |
|---|---|---|---|
| 2,852,473 | 9/1958 | Welling | 252/451 |
| 3,502,595 | 3/1970 | Johnson et al. | 252/455 R |
| 3,770,618 | 11/1973 | Adams et al. | 252/455 R |
| 3,840,477 | 10/1974 | Braithwaite et al. | 252/455 R |
| 3,941,819 | 3/1976 | Vannice et al. | 260/449 R |
| 3,944,503 | 3/1976 | Suto et al. | 252/455 R |

*Primary Examiner*—W. J. Shine
*Attorney, Agent, or Firm*—Morgan, Finnegan, Pine, Foley & Lee

[57] ABSTRACT

A method for the production of dimethyl ether by catalytical reaction between carbon monoxide and hydrogen is disclosed, in which an improved catalyst system is used. The improved catalyst is composed of a mixture of oxides and/or salts of metals such as Al, Cr, La, Mn, Cu, Zn and their mixtures which have been subjected to a stabilization process with a compound of silicon having substituents of various natures; such as hydrocarbonaceous radicals, and halogens. This catalyst is a considerable advance over the prior art.

6 Claims, No Drawings

CATALYST FOR THE PREPARATION OF DIMETHYL ETHER

This invention relates to a method for the preparation of dimethyl ether and to a catalyst which can be used in this method with advantage.

It is known that it is possible to produce dimethyl ether by reacting carbon monoxide with hydrogen.

The main products of the reaction, in addition to dimethyl ether, are methanol, carbon dioxide and water, which accompany the unreacted gas fractions.

The reaction is carried out, as a rule, in the presence of a complex catalyst system which comprises oxygenated derivatives of those elements which are generally used in the synthesis of methanol and in the dehydration reactions.

The book "Catalysis," Vol. III, pages 356-380, by P. H. Emmett, Rheinold Publishing Corp., 1955, detailedly describes the systems proposed for the synthesis of methanol.

Catalyst systems for the synthesis of dimethyl ether have been disclosed as long ago as 1927 in the French patent specification No. 641,580. An example of a method useful for the production of dimethyl ether has also been given in the Italian patent specification No. 927,655 owned by the Assignee hereof.

The catalyst systems as described hitherto give fair results as regards the yields and the conversion to dimethyl ether, but have the defect that their active life is short and does not permit a commercial exploitation of the methods.

In the U.S. patent application Ser. No. 633,859, filed Nov. 20, 1975, now abandoned, a method is disclosed for the preparation of such ether starting from alcohols and in which a catalyst is used which is composed of active alumina which has been modified by reacting it with silicon compounds.

It can be said that, even though such a catalyst permits the production of dimethyl ether from methanol, it has, however, the considerable drawback of requiring the preliminary preparation of methanol with comparatively low yields per pass over the catalyst so that recoveries, recycling and product separations become necessary.

In addition, even with methanol as the starting material, the catalyst described in the above cited patent application while having an acceptable service life, is incapable of affording methanol conversion ratings above 84% under the most favorable conditions.

Summing up, the conventional catalysts either have unsatisfactory service lives, or are incapable of giving acceptable conversion ratings and, in some instances have both defects.

It has now been found, and this is the subject matter of this invention, that dimethyl ether can be produced with high yields and high conversion ratings by using a catalyst which has, under the reaction conditions, a service life sufficiently long to permit a profitable exploitation thereof from a commercial standpoint.

More particularly, the catalysts of this invention are stable under the reaction conditions and can be used in the dimethyl ether synthesizing process for periods as long as several thousands of hours.

The method which is the subject of the present invention comprises the steps of feeding to a reaction enclosure a gaseous mixture composed of $CO$, $H_2$ and possibly also $CO_2$ and reacting $CO$ and $H_2$ within said enclosure in the presence of the catalyst to be described hereinafter. The dimethyl ether is obtained with quantitative yields and is recovered from the mixture emerging from the reactor with conventional means.

The catalysts according to the present invention are composed of metal oxides and/or salts which have undergone a stabilization process.

The phrase "stabilization process" is intended herein to connote a chemical treatment to which the catalyst is subjected, or a few components of the catalyst are subjected, in order to make it capable of withstanding heat and mechanical stresses as well as the action of steam at high temperatures.

More particularly, a treatment with silicon compounds can be adopted with advantage, of the kind disclosed for the stabilization of alumina in the Italian patent specification No. 1,001,614 and in the U.S. patent application Ser. No. 519,791, now U.S. Pat. No. 4,013,589, owned by the Assignee hereof. They correspond to the general formula:

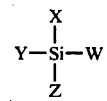

wherein X, Y, Z, W can be —R, —OR, —Cl, —Br, —SiH$_3$, —COOR, —SiH$_n$Cl$_m$ in which R can be hydrogen, an alkyl, cycloalkyl, aromatic, alkyl aromatic or alkylcycloalkyl radical having from 1 to 30 carbon atoms, more particularly methyl, ethyl, isopropyl, nor.-propyl, nor.butyl, isobutyl, cyclohexyl, cyclopentyl, phenyl, phenylcyclohexyl, alkylphenyl, and n and m are numbers from 1 to 3.

The term "mixtures of metal oxides and metal salts is intended to indicate those compositions which comprises oxides or salts of aluminum, chromium, lanthanum, manganese, copper, zinc and mixtures thereof.

The presence of aluminum in the catalyst mixture is critical since the stabilizing effect of the silicon derivatives is unfolded especially on the aluminum oxide, so that an atomic contents of 10% to 70% of aluminum is required in order that the catalyst may have the characteristics which are necessary to keep the catalyst activity unaltered for long periods of time.

The combination of the metal oxides or salts can be obtained with the technical conventional procedures, whereas the stabilization can be carried out either before or after having admixed all the ingredients together.

By way of example, it is possible to co-precipitate by variation of the pH all the metals which compose the catalyst, starting from a solution of their salts (more particularly nitrates or acetates).

The precipitate, upon collection on a filter and washing, is dried and fired at 400° C. and then powdered. An as alternative to nitrates and acetates, it is possible, for example, to use mixtures of basic carbonates, oxides and hydroxides of metals.

As an alternative to drying, the filter can be slurried in water again after washing and then atomized. The catalyst powder thus obtained can be treated with the silicon compounds, such as tetraethyl orthosilicate, at a temperature of from 0° C. to 120° C., the excess silicon compound being removed by heating above 170° C.

The catalysts so stabilized are subsequently subjected to shaping with the conventional procedures such as extrusion, tabletting, pelletizing and so on.

The treatment with tetraethylorthosilicate can be carried out, as an alternative, before firing or after the catalyst shaping and can be replaced if necessary.

Another method of preparation can comprise the steps of separately precipitating the oxides of the metal which compose the catalyst, with the exclusion of alumina, and, upon drying and atomizing, admixing them with the aluminum oxide which has been stabilized by the treatment with silicon derivatives such as tetraethyl orthosilicate, silicon tetrachloride and others.

The admixture with the stabilized aluminum oxide can be carried out also after firing.

The thus obtained catalyst, prior to unfolding its full activity, must appropriately be reduced, by having a mixture of hydrogen, possibly diluted with nitrogen, flowing over the catalyst bed at temperature which are gradually increased until reaching the preselected reaction temperature. Reduction times and temperatures will be selected as a function of the formation which has been prepared.

Without delving into the mechanism of the reaction and without thereby limiting the invention, it is surmised that the dimethyl ether synthesizing reaction does not involve, of necessity, the intermediate formation of free methanol in the gaseous phase. The reaction can be conducted over a wide range of temperatures and pressures. More particularly, it has proven an asset to operate between 30 and 400 atm and between 200° C. and 500° C., the range from 40 atm to 150 atm and from 230° C. to 350° C. being preferred.

The ratios between the reagents are not particularly critical: it has been ascertained, however, that it can be an advantage to work with molar ratios $CO/H_2$ comprised between 1:10 and 3:1. The spatial velocity can be varied, preferentially, between 1,000 hours$^{-1}$ and 10,000 hours$^{-1}$ but also with higher spatial velocities satisfactory results can be obtained.

The reaction mixture can also contain gases which are inert to the reaction concerned.

The following Examples illustrate the invention without limiting same.

Prior to describing the Examples, a few definitions will be given.

DEFINITIONS

CO conversion in mol % =
$$\frac{\text{(Fed-in CO moles)} - \text{(Unreacted CO moles)}}{\text{(Fed-in CO moles)}} \times 100$$

DME selectivity in mol % =
$$\frac{2 \times \text{(Produced DME moles)}}{\text{(Fed-in CO moles)} - \text{(Unreacted CO moles)}} \times 100$$

$CH_3OH$ Selectivity in mol % =
$$\frac{\text{(Produced CH}_3\text{OH moles)}}{\text{(Fed-in CO moles) Unreact. CO moles)}} \times 100$$

$CO_2$ Selectivity in mol % =
$$\frac{\text{(Produced CO}_2\text{ moles)}}{\text{(Fed-in CO moles)} - \text{(Unreacted CO moles)}} \times 100$$

DME = dimethyl ether

EXAMPLE 1

There has been prepared according to the procedure to be detailed below, a catalyst based on Cu, Zn, Cr and Al, these metals being present in atomic ratios equal to 20/12/8/60.

1,600 Grams of $Cu(NO_3)_2.3H_2O$, 17180 grams of $Zn(NO_3)_2.6H_2O$ and 1,060 grams of $Cr(NO_3)_3.9H_2O$ are dissolved in 20 liters of water. The solution is heated to 85° C. and there are added thereto, with stirring, 20 liters of a solution obtained by dissolving 1,300 grams of NaOH in water. The precipitate is allowed to settle upon cooling, is washed with water by decantation, collected on a filter and washed with water again. The precipitate is oven dried at 120° C.

The material is ground until granules are obtained which are not coarser than 20-mesh A.S.T.M., then it is admixed with 1,000 grams of gamma-alumina having a grit size between 20-mesh and 100-mesh A.S.T.M. as prepared according to the procedure disclosed in EXAMPLE 1 of the Italian patent specification No. 1,001,614.

The composition is tabletted until tabloids are obtained having a diameter of 4 millimeters and a length of 6 millimeters.

100 mls of such a catalyst have been charged in a tubular reactor having a diameter of 254 millimeters which has been placed in an electrically heated tubular oven. Axially in the center of the reactor a thermocouple sheath is positioned, which has an outside diameter of 8 millimeters.

The temperature has gradually been raised by feeding to the reactor a mixture of hydrogen and nitrogen in order to reduce the catalyst under controlled conditions. As the temperature has attained 260° C. and no more heat build-up has been detected, as due to the reaction of reduction of the catalyst, the pressure has been raised to 50 kilograms/sq.centimeter and the hydrogen-nitrogen mixture has gradually been replaced by a mixture of CO and $H_2$ in the ratio of 25% CO and 75% $H_2$ at a spatial velocity of 3,500 hours$^{-1}$. The temperature of the catalyst had meanwhile been stabilized to 300° C.

By a condenser placed downstream of the reactor, methanol and water have been condensed along with a portion of the dimethyl ether as produced in the reactor. Water, methanol and condensed dimethyl ether have been withdrawn from the installation under pressure and analyzed. The gases emerging from the reactor have been caused to pass through the sampling valve of a chromatograph, analyzed and then sent to a flowmeter to measure the rate of flow.

TABLE 1 tabulates the results of a duration test which has been conducted under the conditions described above for 475 hours. The by-products which were present in concentrations below 1% have not been considered.

EXAMPLE 2 (COMPARISON TEST)

A catalyst having the same composition as EXAMPLE 1 and prepared with the procedure described therein, but in which the stabilized gamma-alumina has been replaced by non-stabilized gamma-alumina has been subjected to a duration test under the conditions described in EXAMPLE 1. The results are tabulated in TABLE 2.

The present Example has been reported for comparison purposes and shows that the conversion of CO and the DME selectivity decay with the lapse of time when no stabilized gamma-alumina is used.

TABLE 1

| Hours (Progress.) | Co-conversion mol % | SELECTIVITY, IN, %, OF CO CONVERTED INTO | | |
|---|---|---|---|---|
| | | DME | $CH_3OH$ | $CO_2$ |
| 2 | 62 | 61.4 | 3.2 | 35.4 |
| 9 | 61 | 61.1 | 2.9 | 36 |
| 27 | 59 | 62.3 | 2.8 | 34.9 |
| 54 | 58 | 61.8 | 2.7 | 35.5 |
| 86 | 59 | 63.2 | 2.9 | 33.9 |
| 115 | 57 | 62.7 | 3.1 | 34.2 |
| 118 | 58 | 60.8 | 3.0 | 36.2 |
| 264 | 56 | 61.6 | 2.9 | 35.5 |
| 350 | 56 | 61.3 | 3.3 | 35.4 |
| 475 | 57 | 62.1 | 3.1 | 34.8 |

TABLE 2

| Hours (Progress.) | Co-conversion mol % | SELECTIVITY, IN % OF CO CONVERTED INTO: | | |
|---|---|---|---|---|
| | | DME | $CH_3OH$ | $CO_2$ |
| 2 | 64.3 | 59.7 | 3.9 | 36.4 |
| 7 | 63.6 | 58.9 | 3.5 | 37.6 |
| 24 | 64.1 | 59.4 | 3.8 | 36.8 |
| 48 | 63.8 | 58.8 | 6.7 | 34.5 |
| 92 | 60.1 | 54.3 | 11.4 | 34.3 |
| 127 | 55.4 | 52.7 | 14.7 | 32.6 |
| 164 | 51.7 | 48.6 | 18.1 | 33.3 |
| 198 | 42.3 | 44.4 | 23.8 | 31.8 |
| 249 | 33.6 | 40.7 | 29.5 | 29.8 |
| 310 | 24.9 | 31.6 | 38.2 | 30.2 |

EXAMPLE 3

A catalyst has been prepared in which Cu, Zn and Cr are in the atomic ratio of 25/37/38. For this purpose, there are dissolved, in 20 liters of water, 800 grams of $Cu(NO_3)_2.3H_2O$, 1,500 grams of $Zn(NO_3)_2.6H_2O$ and 2,050 grams of $Cr(NO_3)_3.9H_2O$. This solution is heated to 85° C. and, with stirring, the precipitation of the oxides is carried out by adding a 10% aqueous solution of $Na_2CO_3$ until a pH of 7.0–7.2 is reached. Upon cooling, the precipitate is washed with water by decantation, collected on a filter, washed manually with water and oven dried at 120° C. The mass is tabletted so as to obtain tabloids having a diameter of 3 millimeters and a length of 5 millimeters. This catalyst is admixed with an identical quantity (weight basis) of stabilized gamma-alumina in spherules having 3 millimeters of diameter, prepared according to the Example of the Italian patent specification No. 1,001,614. 100 mls of this solid mixture have been used for carrying out an endurance test under the conditions and according to the procedure described in Example 1 hereof, but under a pressure of 90 kilograms per sq. centimeter and with a rate of flow of the CO and $H_2$ mixture of 500 normal liters an hour. The temperature of the reaction was 330° C. The results are tabulated in TABLE 3.

TABLE 3

| Hours (progress.) | Conversion of CO Mol % | SELECTIVITY in %, on the CO converted into: | | |
|---|---|---|---|---|
| | | DME | $CH_3OH$ | $CO_2$ |
| 1 | 48.7 | 44.0 | 18.6 | 37.4 |
| 5 | 46.9 | 46.7 | 16.6 | 36.7 |
| 24 | 45.4 | 48.3 | 15.9 | 35.8 |
| 48 | 49.7 | 47.5 | 14.9 | 37.6 |
| 96 | 46.2 | 48.4 | 17.2 | 34.4 |
| 148 | 44.7 | 48.2 | 18.2 | 33.6 |
| 255 | 43.9 | 47.1 | 17.4 | 35.5 |
| 360 | 44.1 | 48.1 | 16.8 | 35.1 |
| 485 | 42.8 | 47.6 | 19.2 | 33.2 |

EXAMPLE 4

A catalyst is prepared according to the procedure described in EXAMPLE 1 hereof, but employing such quantities of reagents that the atomic ratio Cu, Zn, Cr, Al is equal to 15/10/5/70.

The endurance test is conducted according to EXAMPLE 1 but under a pressure of 90 kgs/sq.cm and at a reaction temperature of 310° C.

In the following the performances of the fresh catalyst, and of the catalyst after a 500-hour run are reported.

| CATALYST | FRESH | AFTER 500 HOURS |
|---|---|---|
| CO-conversion in mol % | 49.7 | 48.2 |
| DME Selectivity, % | 60 | 59.9 |
| $CH_3OH$ selectivity, % | 4.7 | 4.6 |
| $CO_2$ selectivity, % | 35.3 | 35.5 |

EXAMPLE 5

A catalyst is prepared, which has the same composition as EXAMPLE 1 and with the same procedure as that of such Example, but using a stabilized gamma-alumina obtained according to the procedure of EXAMPLE 10 of the Italian patent specification No. 1,001,614.

The endurance test has been conducted as indicated in EXAMPLE 1 hereof but under a pressure of 70 kgs.sq.cm, a rate of flow of 350 normal liter an hour of CO AND $H_2$ and the reaction temperature was 280° C. The performance of the catalyst at the test start and after a 496-hour run are as follows:

| CATALYST | FRESH | AFTER 496 HOURS |
|---|---|---|
| CO-conv. in mol % | 45.9 | 46.7 |
| DME-select., % | 58.8 | 54.8 |
| $CH_3OH$-select., % | 6.7 | 8.7 |
| $CO_2$-select., % | 34.5 | 36.5 |

EXAMPLE 6

In 20 liters of water at 85° C. there are dissolved 1,449 grams of $Cu(NO_3)_2.3H_2O$, 960.4 grams of $Cr(NO_3)_3.9H_2O$, 1.071 grams of $Zn(NO_3)_2.6H_2O$ and 3.000.1 grams of $Al(NO_3)_3.9H_2O$, in such a way that the atomic ratio Cu/Zn/Cr/Al is 30/18/12/40.

To the solution which has been so obtained, there is added ammonia, still at 85° C., until a pH of 7.2 is reached, whereafter the precipitate is collected on a filter and washed, re-slurried in water and dried by atomizing. The dry powder thus obtained is treated with tetraethyl orthosilicate according to the procedure suggested in the Italian patent specification No. 1,001,614 whereafter, upon removal of the excess of tetraethyl orthosilicate, the mass is tabletted so as to obtain tabloids having a diameter of 4 millimeters and a length of 6 millimeters.

The thusly obtained catalyst is fired at 350° C., 100 mls of the catalyst are charged in the reactor described in EX. 1 hereof and reduced with the precautions suggested in that Example. A reaction mixture is then fed-in, which is composed of 75% of hydrogen and 25% carbon monoxide, at a temperature of 320° C. and under a pressure of 90 atm at a spatial velocity of 7,500 hours$^{-1}$. Endurance tests have been performed for a period of 540 hours and the initial and final performance are as follows:

| CATALYST | FRESH | AFTER 540 HOURS |
|---|---|---|
| CO-convers.mol % | 65.80 | 64.15 |
| DME-selectivity, % | 68.72 | 62.82 |
| $CH_3OH$-selectiv., % | 2.96 | 3.20 |
| $CO_2$-selectiv., % | 33.32 | 33.28 |

EXAMPLE 7

Over the same catalyst as in EXAMPLE 1, there is fed a 50% by volume mixture of carbon monoxide and 50% by volume of hydrogen at a spatial velocity of 3,500 hours$^{-1}$, under a pressure of 90 atm and at a temperature of 300° C. In the following, there are reported the performances of the fresh catalyst and of the catalyst after 580 hours of use.

| CATALYST | FRESH | OVER 580 HOURS |
|---|---|---|
| CO-conversion, % mol | 53 | 51.9 |
| DME-selectivity, % | 63.8 | 62.9 |
| $CH_3OH$-selectivity, % | 1.9 | 3.0 |
| $CO_2$-selectivity, % | 34.3 | 34.1 |

We claim:

1. A catalyst for the production of dimethyl ether consisting essentially of a mixture of an oxide of aluminum with at least one other oxide selected from the group consisting of the oxides of chromium, lanthanum, manganese, copper and zinc, wherein the atomic content of said aluminum is in the range of 10% to 70% and at least said aluminum oxide is stabilized by means of a silicon compound containing hydrolyzable groups selected from the group represented by the formula:

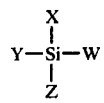

wherein X, Y, Z and W represent —R, —OR, —Cl, —Br, —$SiH_3$, —COOR, —$SiH_nCl_m$, in which R is a member of the group consisting of hydrogen, alkyl, cycloalkyl, aromatic, alkylaromatic, and cycloalkyl having from 1 to 30 C atoms, and n and m represent numbers from 1 to 3, through a thermal treatment wherein said aluminum oxide is impregnated with the silicon compound and then heated in an inert atmosphere to the boiling temperature of the silicon compound so as to react the silicon compound with the aluminum oxide and distill off reaction products and excess silicon compound and thereafter heated in the present of steam so as to react hydrolyzable groups bound to silicon with water.

2. A catalyst as claimed in claim 1, wherein the aluminum oxide is mixed with oxides of copper, zinc and chromium.

3. A catalyst as claimed in claim 1, wherein the aluminum oxide is stabilized gamma-alumina.

4. A catalyst as claimed in claim 1, wherein the radical R is a member of the group consisting of methyl, ethyl, isopropyl, N-propyl, N-butyl, isobutyl, cyclohexyl, cyclopentyl, phenyl, phenyl-cyclohexyl and alkylphenyl.

5. A catalyst as claimed in claim 1, wherein each oxide in said mixture is stabilized by means of said silicon compound through said thermal treatment.

6. A catalyst as claimed in claim 1 wherein said aluminum oxide is spheroidal gamma alumina.

* * * * *

UNITED STATES PATENT AND TRADEMARK OFFICE
CERTIFICATE OF CORRECTION

PATENT NO. : 4,177,167
DATED : December 4, 1979
INVENTOR(S) : Giovanni Manara, et al.

It is certified that error appears in the above-identified patent and that said Letters Patent are hereby corrected as shown below:

Col. 2, lines 58 and 59, change "An as" to read --As an--.

Col. 5, line 2, in the heading, change "SELECTIVITY, IN, %," to read --SELECTIVITY, IN %,--

Col. 8, line 21 (second to the last line of Claim 1), change "present" to read --presence--.

Signed and Sealed this

Twenty-ninth Day of April 1980

[SEAL]

Attest:

SIDNEY A. DIAMOND

Attesting Officer   Commissioner of Patents and Trademarks